United States Patent
Han (10) Patent No.: US 7,033,101 B2
(45) Date of Patent: Apr. 25, 2006

(54) INTERPROXIMAL BRUSH WITH GARGLE AND DISINFECTANT

(76) Inventor: Sang Kee Han, #5-902 Asia Seonsoochon Apt. 86 Jamsil-dong, Songpa-gu, Seoul (KR)

( * ) Notice: Subject to any disclaimer, the term of this patent is extended or adjusted under 35 U.S.C. 154(b) by 0 days.

(21) Appl. No.: 10/214,015

(22) Filed: Aug. 6, 2002

(65) Prior Publication Data

US 2003/0231918 A1    Dec. 18, 2003

(30) Foreign Application Priority Data

Jun. 14, 2002 (KR) .................. 10-2002-0033381
Jun. 14, 2002 (KR) .................. 20-2002-0018131

(51) Int. Cl.
A46B 11/00 (2006.01)
B05C 1/00 (2006.01)

(52) U.S. Cl. .................. 401/129; 401/126; 401/122; 401/17

(58) Field of Classification Search .................. 401/17, 401/18, 24, 34, 35, 127, 129, 122, 268, 126; 132/310
See application file for complete search history.

(56) References Cited

U.S. PATENT DOCUMENTS

| | | | | |
|---|---|---|---|---|
| 1,914,240 A | * | 6/1933 | Caldwell | 132/310 X |
| 2,095,741 A | * | 10/1937 | Hachman | 132/310 X |
| 2,550,586 A | * | 4/1951 | Nardone | 401/129 |
| 4,600,328 A | * | 7/1986 | Clements | 401/17 X |
| 5,620,270 A | * | 4/1997 | Gueret | 401/126 |
| 5,834,427 A | | 11/1998 | Han et al. | |
| 6,276,853 B1 | * | 8/2001 | Breidenbach et al. | 401/18 X |
| 2001/0054211 A1 | * | 12/2001 | Cabedo-Deslierres et al. | 132/310 X |

FOREIGN PATENT DOCUMENTS

| | | | |
|---|---|---|---|
| GB | 2231782 | * 11/1990 | 401/268 |
| KR | 20-0246271 | 8/2001 | |

* cited by examiner

Primary Examiner—David J. Walczak
(74) Attorney, Agent, or Firm—Intellectual Property Law Group LLP; Otto O. Lee; Juneko Jackson (57) ABSTRACT

An embodiment of the invention is an interproximal brush with gargle and disinfectant. This interproximal brush includes two brush units. The brush units each consists of a handle having a rectangular cross-section, and an interproximal cleaning means, such as bristles or a dental floss, fixed to an end of the handle. The interproximal brush also has a casing consisting of two reception parts. In this case, the reception parts have a hollow box shape for receiving the brush units, and contain gargle and disinfectant therein, respectively. Further, a sealing unit is provided at a position around a mouth of each of the two reception parts.

17 Claims, 9 Drawing Sheets

INTERPROXIMAL BRUSH WITH GARGLE AND DISINFECTANT

BACKGROUND OF THE INVENTION

1. Field of the Invention

The present invention relates generally to an interproximal brush, and more particularly, to an interproximal brush which contains gargle and disinfectant, such as mouthwash, thus accomplishing an excellent cleaning effect in addition to protecting the gingiva while brushing a gap between neighboring teeth.

2. Description of the Prior Art

As well known to those skilled in the art, an interproximal brush is used for brushing a gap between neighboring teeth, and consists of a handle, and dental floss or bristles shaped like bristles of a brush for cleaning test tubes. In this case, the bristles or the dental floss are fixed to the end of the handle. That is, the interproximal brush is an article for cleaning the gap between neighboring teeth by repeatedly putting and taking the bristles or the dental floss in and out of the gap between the neighboring teeth. Such an interproximal brush is used in a location where it is difficult to remove plaque or food residue remaining in a user's mouth with a general type toothbrush. The interproximal brush is also used for disinfecting the teeth after scaling, and for removing tartar deposited on the teeth due to smoking. Further, the interproximal brush is used to clean orthodontic devices, such as braces for straightening misaligned teeth.

However, the conventional interproximal brush is problematic in that the teeth are brushed using only the bristles, so a user may frequently bleed at the gingiva, and further, it is difficult to remove the food residue remaining in the user's mouth. Generally, this interproximal brush is not disposable and has to be repeatedly reused. Due to its repeated use, the brush may have an offensive odor, or bacteria may be propagated on the brush, so the brush must be frequently disinfected.

Therefore, there has been proposed a conventional interproximal brush in Korean U.M. Registration No. 246271 filed by and allowed to this inventor. This interproximal brush has a reception part of a circular cross-section. The reception part contains a cleaning solution therein, such that bristles of the brush are kept in the cleaning solution when the brush is not used. However, the reception part of the conventional interproximal brush contains only one of several solutions, such as disinfectant, whitener, and calcium dissolving solution. Further, a casing of the interproximal brush has a circular sidewall, so it is difficult to attach anything, including a trademark, to the sidewall of the casing.

SUMMARY OF THE INVENTION

Accordingly, the present invention has been made keeping in mind the above problems occurring in the prior art, An object of the present invention is to provide an interproximal brush, which has a casing consisting of two reception parts such that gargle and disinfectant are contained in the two reception parts, respectively, thus easily cleaning and disinfecting. The embodiment of the present invention is designed to easily supply the gargle and/or the disinfectant to a brushed portion while brushing a gap between neighboring teeth, thus accomplishing an improved cleaning effect in addition to protecting the user's gingiva, and which is designed in such a way as to easily carry several interproximal brushes.

In order to accomplish the above object, the embodiment of the present invention provides an interproximal brush device forming a single structure, comprising two brush units each consisting of a handle having a square cross-section, and an interproximal cleaning means, having bristles or a dental floss, fixed to an end of the handle, and a casing consisting of two reception parts, the reception parts having a hollow box shape for receiving the brush units, and containing gargle and disinfectant therein, respectively, with a sealing unit being provided at a position around a mouth of each of the two reception parts.

According to the embodiment of the present invention, the two reception parts are integrated with each other to form a single structure, and are linearly arranged in a straight line in such a way that the mouths of the reception parts are opposite to each other.

In the embodiment of the present invention, the two reception parts are integrated with each other to form a single structure, and are arranged parallel to each other in such a way that the mouths of the reception parts are adjacent to each other.

In addition, the sealing unit consists of a locking ring with a locking groove provided on the inner circumferential surface of each of the two reception parts at a position adjacent to the mouth of each reception part, and holding the brush unit, and a locking projection provided on the outer circumferential surface of the handle of each brush unit at a midsection thereof.

Further, the sealing unit comprise a rubber or silicone attached to both the inner circumferential surface of each reception part and the outer circumferential surface of the handle of each brush unit.

According to the embodiment of the present invention, an elastic packing member with a hole is provided in a reception part so as to prevent the gargle and the disinfectant from leaking from the reception part. Preferably, the outer circumferential surface of the packing member is fitted into a groove formed on the inner circumferential surface of the casing.

In addition, the handle is provided at one end thereof with bristles or a dental floss and provided at the other end with an opening for receiving another brush unit.

Further, the interproximal brush of this embodiment contains both gargle and disinfectant, and allows a user to carry several brush units.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Reference should now be made to the drawings, in which the same reference numerals are used throughout the different drawings to designate the same or similar components.

Figure 1:
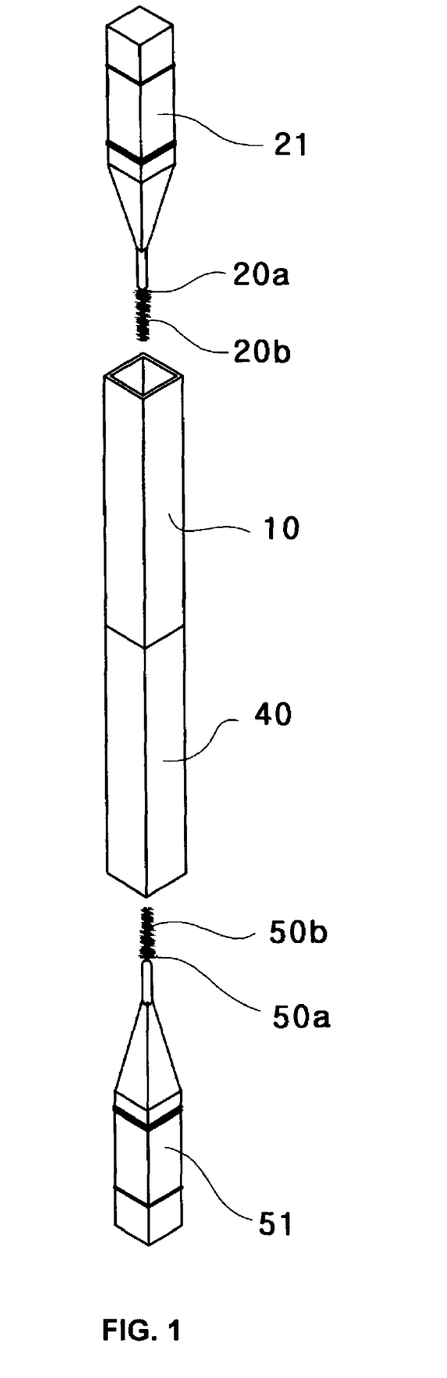
FIG. 1 is an exploded perspective view showing an interproximal brush with gargle and disinfectant according to the primary embodiment of this invention.
Figure 2:
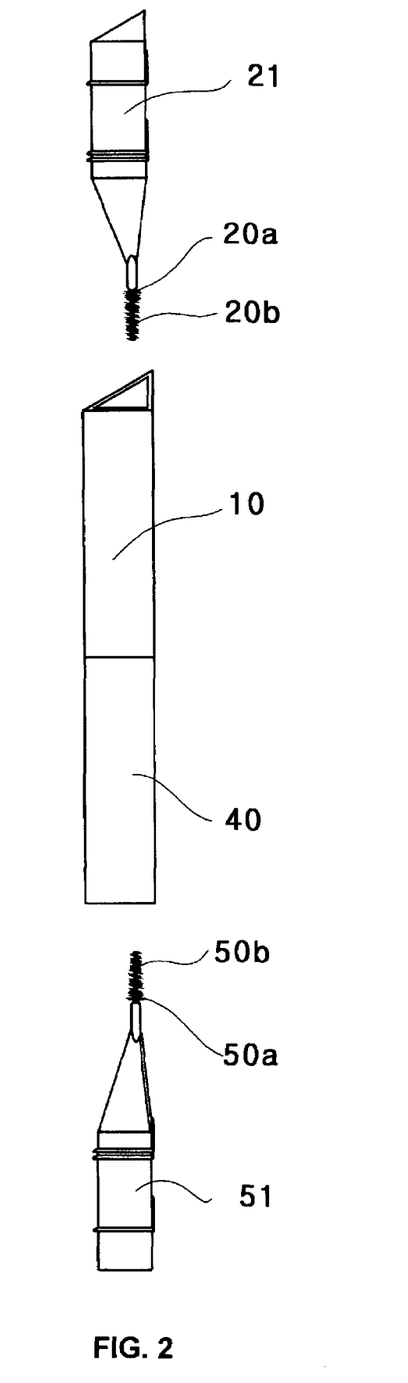
FIG. 2 is an exploded perspective view of an interproximal brush with gargle and disinfectant according to the second embodiment of this invention.
Figure 3:
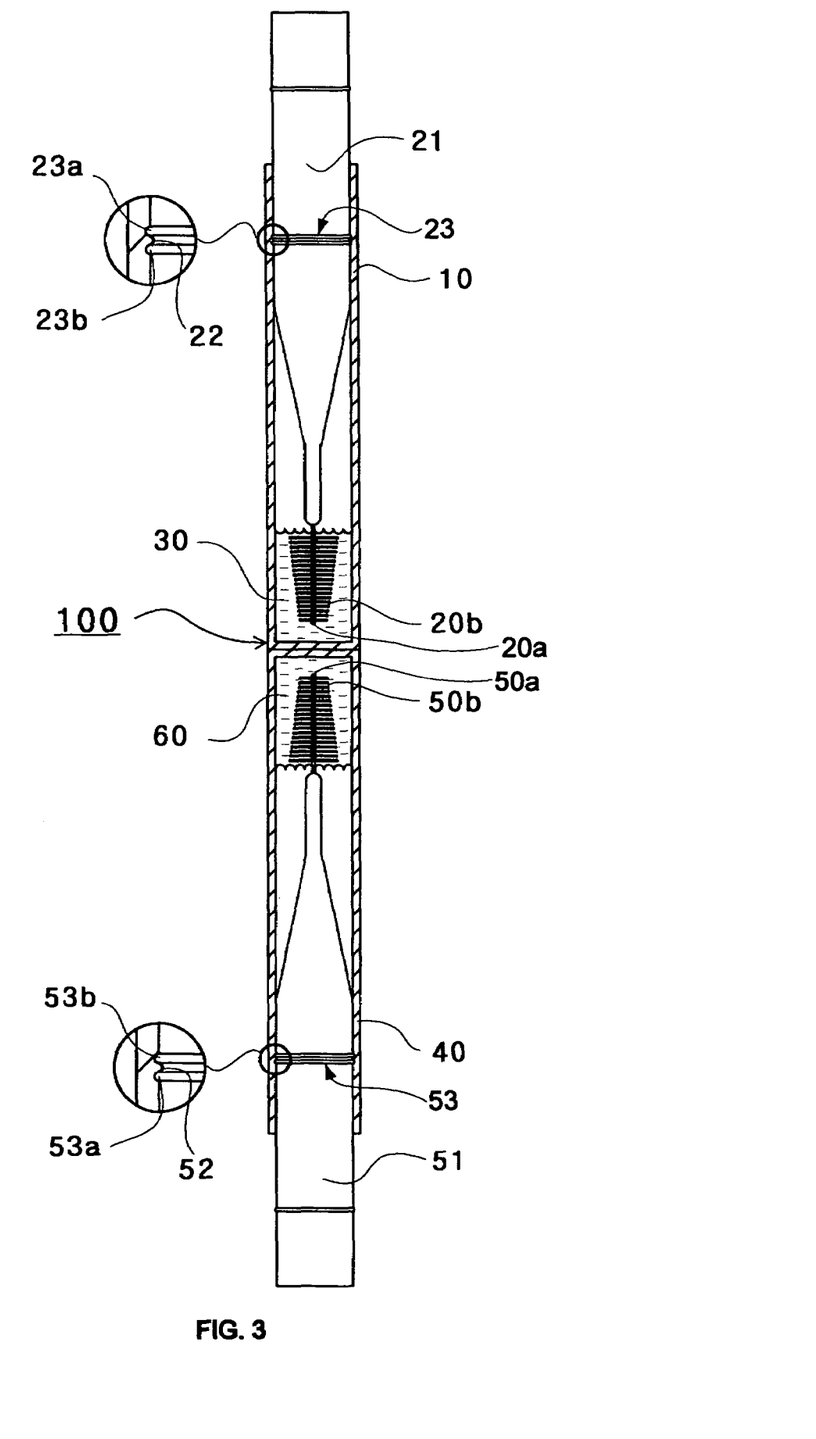
FIG. 3 is a sectional view of the interproximal brush shown in FIG. 1 or FIG. 2, in which brush units of the interproximal brush are received in a casing.

FIG. 1 is an exploded perspective view showing an interproximal brush with gargle and disinfectant according to the primary embodiment of this invention. FIG. 2 is an exploded perspective view of an interproximal brush with gargle and disinfectant according to the second embodiment of this invention. FIG. 3 is a sectional view of the interproximal brush shown in FIG. 1 or FIG. 2, in which brush units of the interproximal brush are received in a casing.

As shown in the drawings, the interproximal brush device includes two brush units and a casing 100. One of the two brush units consists of a handle 21 and bristles 20b, while the other brush unit consists of a handle 51 and bristles 50b. In this case, the handles 21 and 51 have a square cross-section. The bristles 20b are fixed to a core 20a which is provided at an end of the handle 21, and the bristles 50b are fixed to a core 50a which is provided at an end of the handle 51. The casing 100 consists of two reception parts 10 and 40. The two reception parts 10 and 40 have a hollow box shape for receiving the brush units, and contain gargle 30 and disinfectant 60 therein, respectively. The reception parts 10 and 40 are in close contact with the brush units, at the mouths of the reception parts 10 and 40, in order to prevent the gargle 30 and the disinfectant 60 from leaking. Further, the two reception parts 10 and 40 are integrated with each other to form a single structure, and are linearly arranged in a straight line in such a way that the mouths of the reception parts 10 and 40 are opposite to each other.

The cores 20a and 50a are made of plastic or a thin wire. In the case of making the cores 20a and 50a using a thin wire, the wire is preferably made of stainless steel for the prevention of oxidization. Furthermore, it is preferable that the bristles 20b and 50b are made of a material which is soft at a tip and has appropriate elasticity.

The handles 21 and 51 are produced using various kinds of synthetic resins through a molding process, and support the cores 20a and 50a. In addition, the handles 21 and 51 may have insert holes such that the cores 20a and 50a are removably held in the handles 21 and 51, respectively. Further, the cores 20a and 50a may be fixed to the handles 21 and 51 through a welding process, respectively.

A sterile solution containing salt roasted in bamboo, a sterile saline solution, or a mouthwash is used as the gargle 30 contained in the reception part 10. The gargle 30 or disinfectant 60 may contain xylitol, Casein Phosphopeptide (CPP), or Casein Phosphopeptide (CPP-H) disclosed in Korean Patent No. 0140248 filed by and allowed to this inventor. The CPP-H is a substance aiding absorption of calcium contained in milk, and is different from the conventional CPP in the type, sequence and highorder structure of its amino acid. The CPP-H has a more excellent calcium dissolving capacity in comparison with the CPP, thus effectively removing tartar from the teeth. Further, the disinfectant 60 contains an aromatic substance using mint, fruit, or lilac essence, thus allowing a user to feel refreshed.

The reception parts 10 and 40 are made of plastic, and receive the bristles 20b and 50b therein, respectively. A sealing unit is provided at a position around a mouth of each of the reception parts 10 and 40. Preferably, the sealing unit comprises, a locking ring 22 or 52 with two locking grooves provided on the inner circumferential surface of each reception part 10 or 40, and locking projections 23 and 53 provided on the outer circumferential surfaces of the handles 21 and 51, respectively. Due to an engagement of the locking grooves with the locking projections, it is possible to prevent the gargle 30 and the disinfectant 60 from leaking out of the reception parts 10 and 40 and to prevent the bristles 20b and 50b from being undesirably removed from the reception parts 10 and 40. Further, the locking projection 23 consists of an outer locking part 23a and an inner locking part 23b, while the locking projections 53 consists of an outer locking part 53a and an inner locking part 53b. In this case, the outer locking parts 23a and 53a are used for stopping the brush units when they are inserted into the reception parts 10 and 40 by a predetermined depth. Meanwhile, the inner locking parts 23b and 53b are used for preventing the brush units from being undesirably removed from the reception parts 10 and 40. In this case, a variety of structures may be used for the sealing unit, without being limited to the above structure, for locking the handles 21 and 51 in the reception parts 10 and 40 while preventing the gargle 30 and the disinfectant 60 from leaking. For example, a rubber or a silicone may be provided to both the inner circumferential surface of each reception part 10 and 40 and the outer circumferential surface of each handle 21 or 51, that is, the portion where the handle 10 or 40 is in contact with the reception part 21 or 51.

Figure 7:
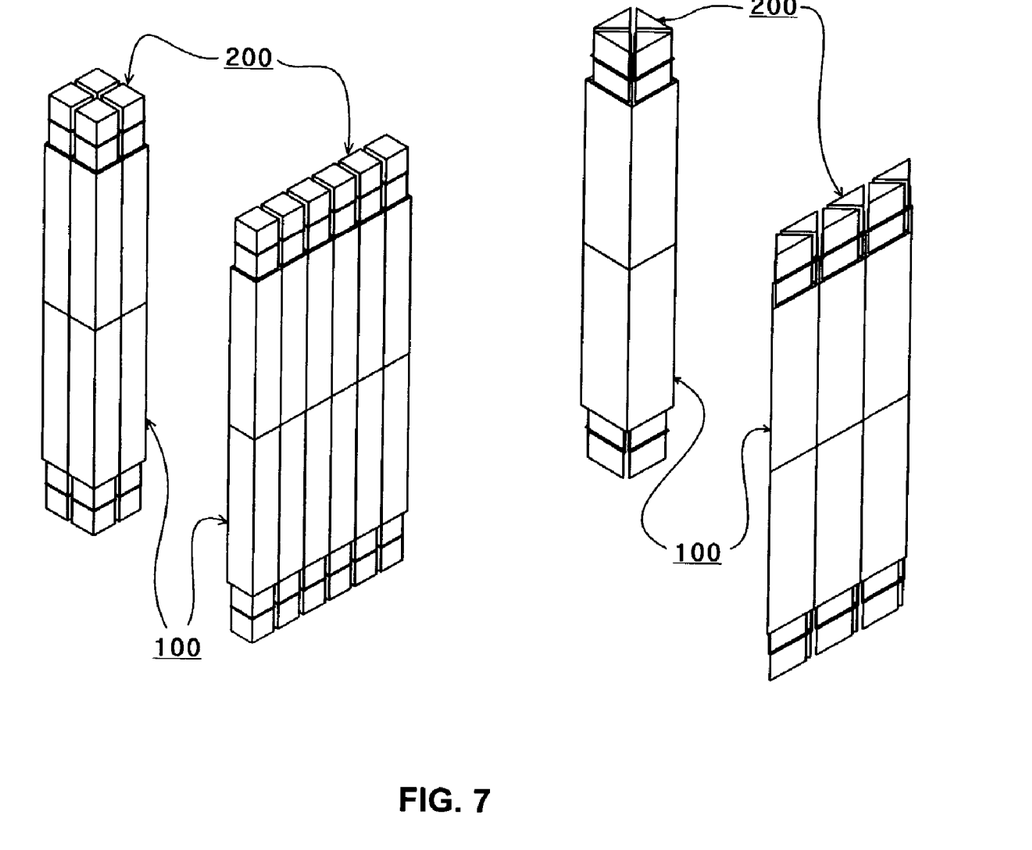
FIG. 7 is a view of the interproximal brush according to the present invention, when the interproximal brush is packaged.

As shown in FIGS. 1 and 2, the reception parts 10 and 40 and the handles 21 and 51 have a square cross-section or a triangular cross-section, resulting in angular corners. When the gargle 30 and/or the disinfectant 60 is almost used up, the gargle 30 and/or the disinfectant 60 is collected on the angular corners, thus completely consuming the gargle 30 and/or the disinfectant 60, therefore being effective and economical to use. Since the sidewall of the casing 10 is flat, anything, including a trademark, can be easily attached to the casing 10. Further, as shown in FIG. 7, a plurality of interproximal brushes may be packaged together in a tetragonal shape or a trapezoid shape, thus allowing for easy and compact storage and packaging in comparison with convention interproximal brushes having rounded sidewalls.

In FIG. 3, the reception part 40 containing the disinfectant 60 is placed upside down. In this case, the disinfectant 60 may be spilled. But, FIG. 3 is only an example used to easily describe the construction of the interproximal brush according to this invention. The interproximal brush of this invention normally lies at a predetermined position, or is placed while repeatedly changing its standing direction. Further, it is possible to use the interproximal brush by shaking it. Thus, the interproximal brush is always covered with the gargle or the disinfectant.

Figure 4:
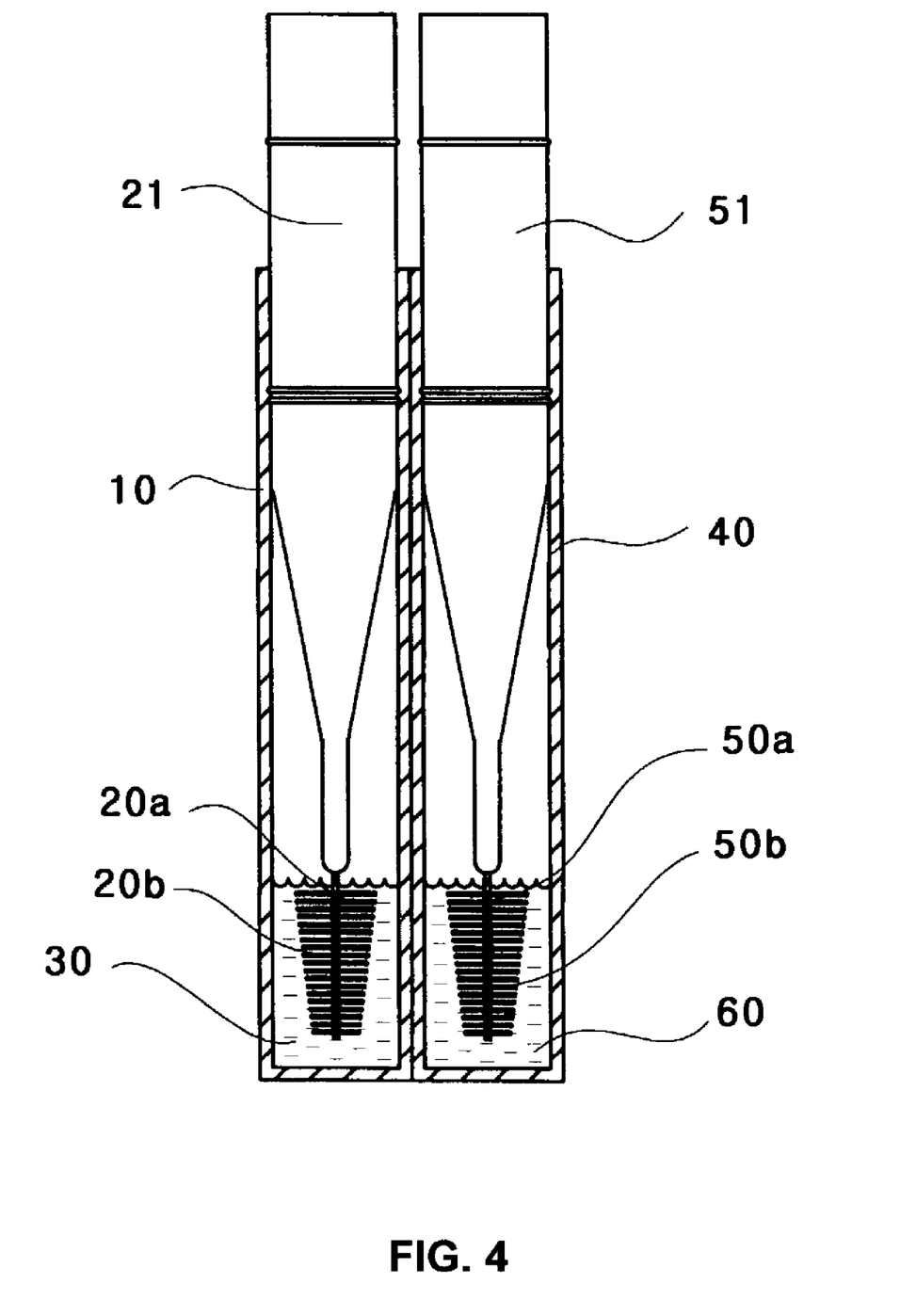
FIG. 4 is a sectional view of an interproximal brush with gargle and disinfectant in accordance with the third embodiment of this invention.

FIG. 4 is a sectional view of an interproximal brush with gargle and disinfectant in accordance with the third embodiment of this invention. In FIG. 4, the reception part 10 containing the gargle 30 and the reception part 40 containing the disinfectant 60 are horizontally arranged parallel to each other.

In this case, in order to easily distinguish the gargle 30 from the disinfectant 60, it is preferable that the casing 10 is made of a transparent material, and that the gargle 30 and the disinfectant 60 have different colors.

When one desires to use the interproximal brush constructed in this way, the gargle 30 and the disinfectant 60 are supplied to the reception parts 10 and 40, respectively. Next, the bristles 20b and 50b are pushed in the reception parts 10 and 40, respectively, until the bristles 20b and 50b are soaked in the gargle 30 and the disinfectant 60. At this time, the inner locking parts 23b and 53b of the handles 21 and 51 pass over the locking rings 22 and 52. The locking ring 22 is locked between the outer and inner locking parts 23a and 23b, while the locking ring 52 is locked between the outer and inner locking parts 53a and 53b, such that the handles 21 and 51 are held in the reception parts 10 and 40, and the gargle 30 and the disinfectant 60 are prevented from leaking out from the casing 10. Further, the bristles 20b and 50b are soaked in the gargle 30 and the disinfectant 60 when the brush is not in use, thus preventing the propagation of bacteria. When one desires to brush a gap between neighboring teeth using the interproximal brush carried with a user, the user catches the reception parts 10 and 40 and pulls the handles 21 and 51 out from the reception parts 10 and 40. At this time, the inner locking parts 23b and 53b pass over the locking rings 22 and 52, and then the handles 21 and 51 are taken out from the reception parts 10 and 40, respectively. In this case, the bristles 20b and 50b are covered with the gargle 30 and the disinfectant 60, respectively, thus enhancing a cleaning effect in addition to protecting the gingiva.

Figure 5:
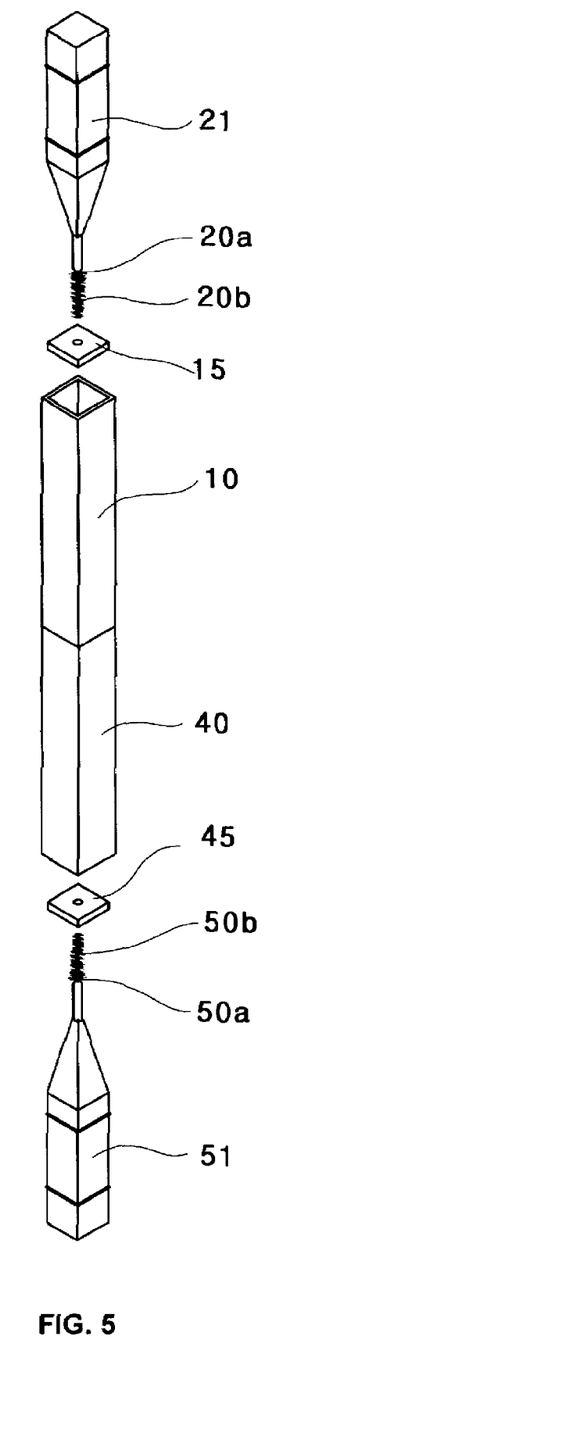
FIG. 5 is an exploded perspective view of an interproximal brush with gargle and disinfectant according to the fourth embodiment of this invention.
Figure 6:
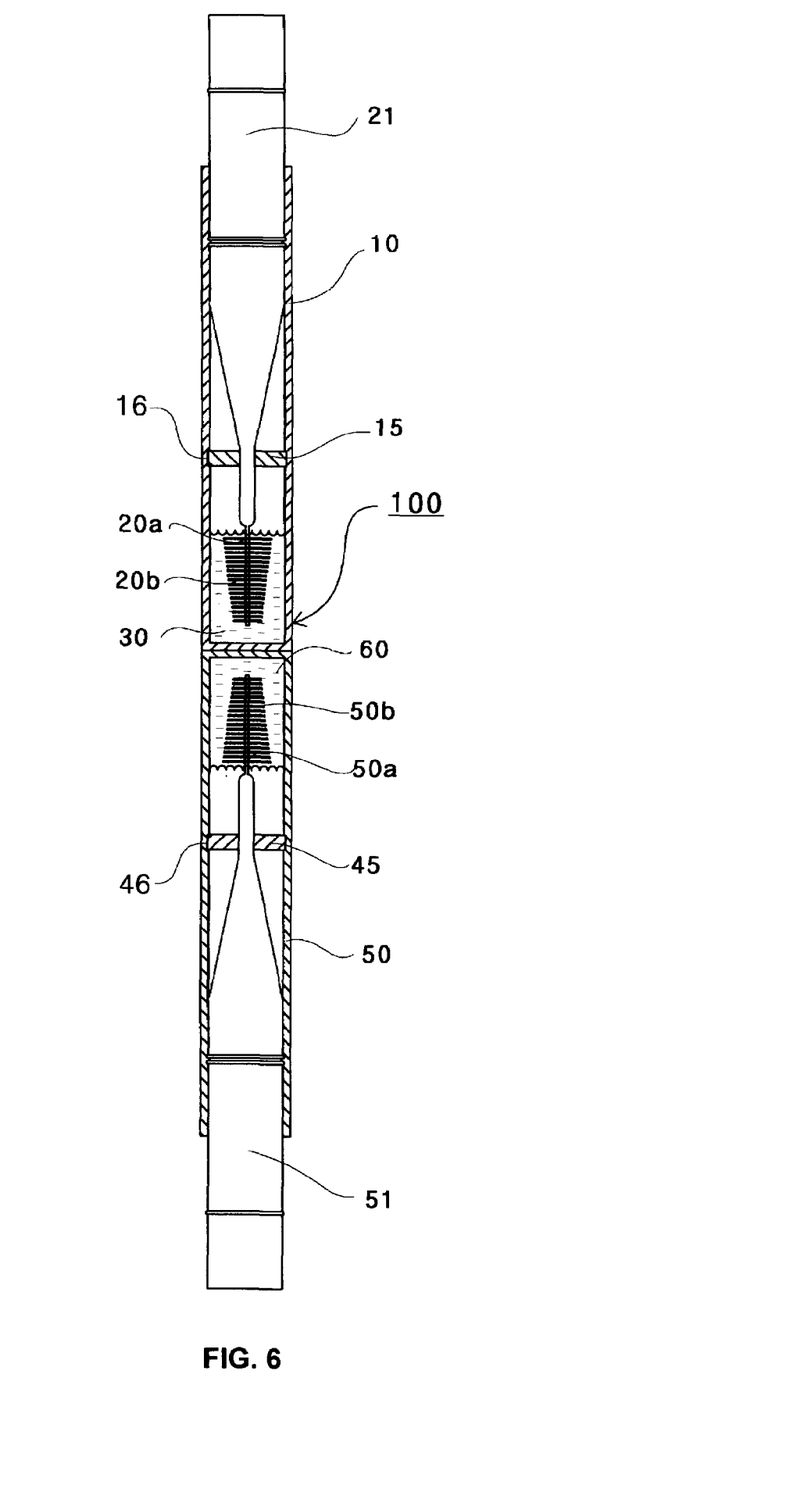
FIG. 6 is a sectional view of the interproximal brush of FIG. 5, in which brush units of the interproximal brush are received in a casing.

FIGS. 5 and 6 show an interproximal brush according to the fourth embodiment of this invention. As shown in the drawings, two packing members 15 and 45 are provided in the two reception parts 10 and 40, respectively, so as to prevent a leakage of the gargle 30 and the disinfectant 60 from the mouths of the reception parts 10 and 40. In this case, there may be several methods of fixing the packing members 15 and 45 to the reception parts 10 and 40. It is preferable that the packing members 15 and 45 made of an elastic material, such as a rubber, are pushed into the reception parts 10 and 40 such that the outer circumferential surfaces of the packing members 15 and 45 are locked to grooves 16 and 46 formed on the inner circumferential surfaces of the reception parts 10 and 40, respectively.

An elastically openable hole is formed on each of the packing members 15 and 45 so as to prevent the gargle 30 and the disinfectant 60 from leaking and to allow the bristles 20b and 50b to be put into and taken out of the reception parts 10 and 40, respectively. That is, the holes of the packing members 15 and 45 are normally constricted. But, when the core 20a with the bristles 20b and the core 50a with the bristles 50b pass through the holes for soaking the bristles 20b in the gargle 30 and soaking the bristles 50b in the disinfectant 60, the diameters of the holes are increased while preventing the gargle 30 and the disinfectant 60 from leaking.

When one desires to use the interproximal brush according to the fourth embodiment, first, a tool, such as a syringe, is inserted into the holes of the packing members 15 and 45 to inject the gargle 30 and the disinfectant 60 into the reception parts 10 and 40, respectively. The handles 21 and 51 are pushed into the reception parts 10 and 40, respectively, until the bristles 20b and 50b are soaked with the gargle 30 and the disinfectant 60 after passing through the holes of the packing members 15 and 45. In this case, the packing members 15 and 45 are made of an elastic material, so they are constricted without a gap, thus preventing the gargle 30 and the disinfectant 60 from leaking. When it is desired to brush a gap between neighboring teeth using the interproximal brush carried with a user, the user catches the reception parts 10 and 40 and pulls the handles 21 and 51 out from the reception parts 10 and 40. At this time, the bristles 20b and 50b fixed to the handles 21 and 51 pass through the holes of the packing members 15 and 45 and then are taken out from the reception parts 10 and 40, respectively. In this case, the food residue remaining in the user's mouth as well as plaque are removed by repeatedly putting the bristles 20b and 50b in and taking the bristles 20b and 50b out of the gap between neighboring teeth. At this time, the bristles 20b and 50b are covered with the gargle 30 and the disinfectant 60, thus effectively removing bacteria and bad breath from the user's mouth without doing harm to the gingiva. In addition, the user can selectively use the bristles 20b with the gargle 30 or the bristles 50b covered with the disinfectant 60, as desired.

Figure 8:
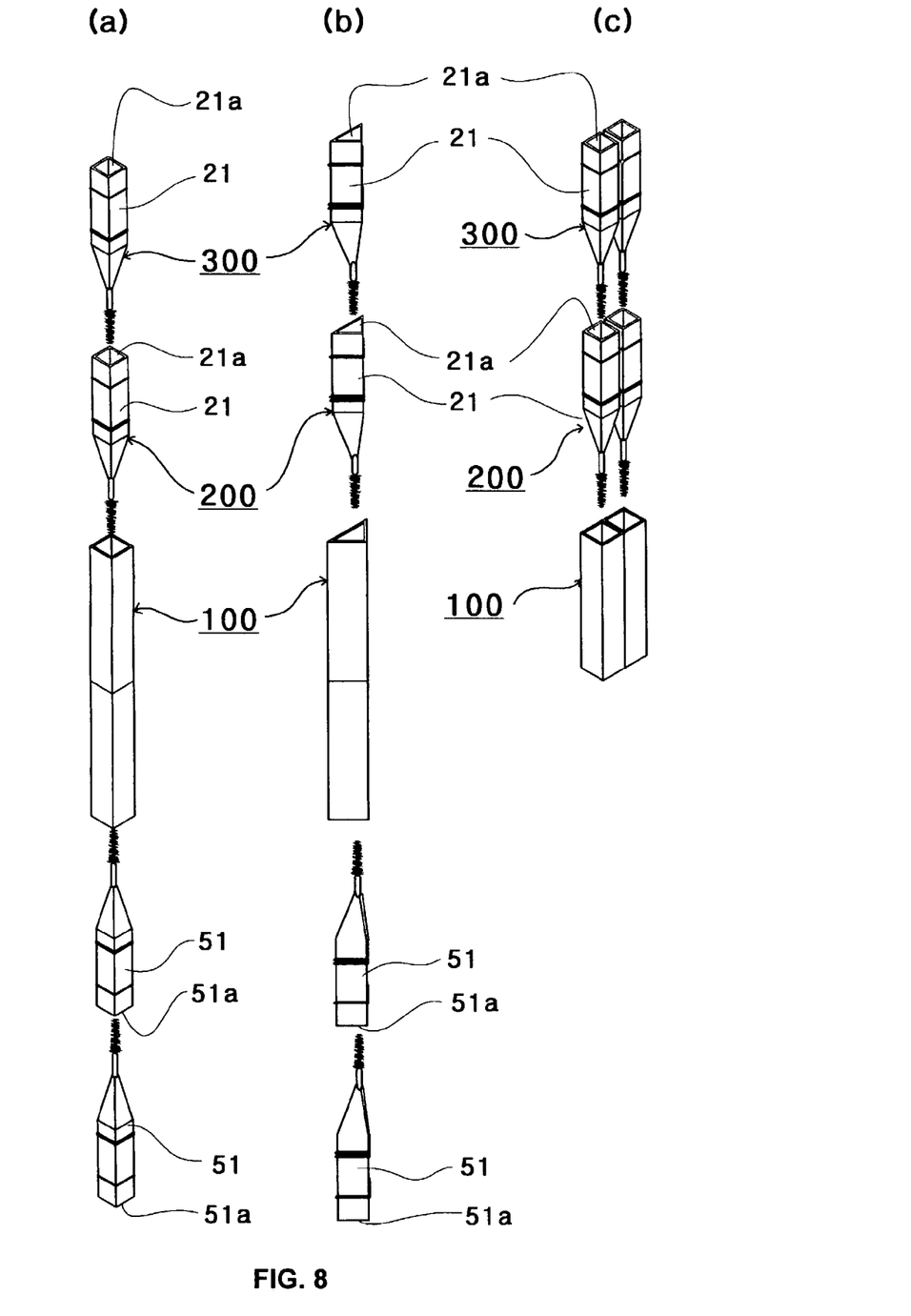
FIGS. 8a to 8c are exploded perspective views showing an interproximal brush with gargle and disinfectant according to the fifth embodiment of this invention.

FIGS. 8a to 8c are exploded perspective views showing an interproximal brush with gargle and disinfectant according to the fifth embodiment of this invention. The handles 21 and 51 of the brush unit 200 are provided at their ends with openings 21a and 51a, respectively, for receiving another brush unit 300. Such a construction allows a user to carry a plurality of brush units at one time, thus easily replacing a broken or worn-out brush unit with a new one.

Figure 9:
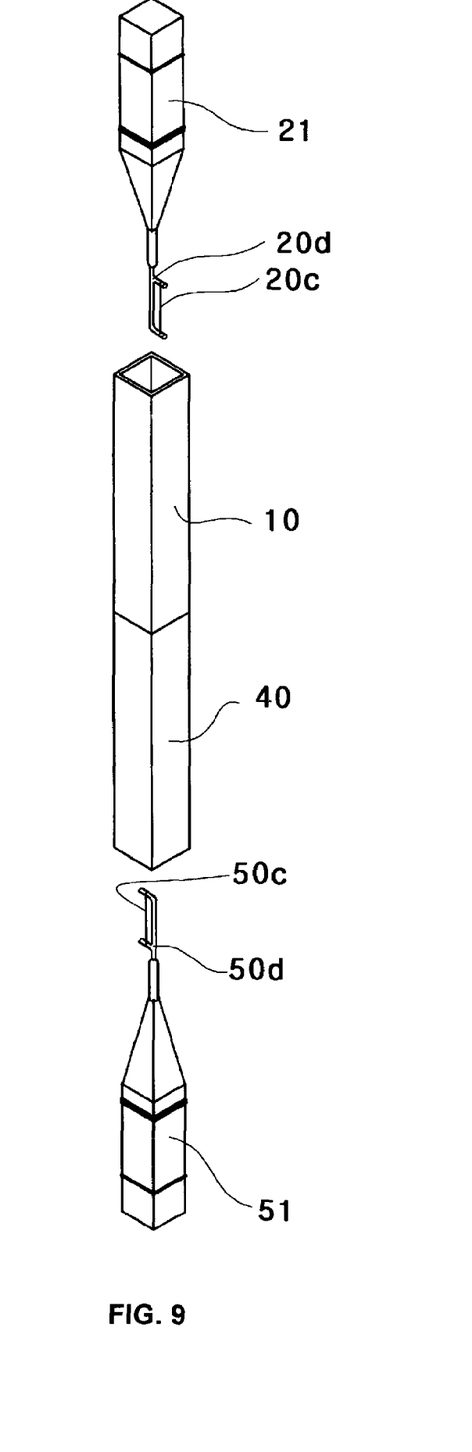
FIG. 9 is an exploded perspective view of an interproximal brush with gargle and disinfectant according to the sixth embodiment of this invention.

FIG. 9 is an exploded perspective view of an interproximal brush with gargle and disinfectant according to the sixth embodiment of this invention. This interproximal brush device includes two brush units and a casing 100. One of the two brush units consists of a handle 21 and a dental floss 20c, while the other brush unit consists of a handle 51 and a dental floss 50c. In this case, the handles 21 and 51 have a square cross-section, respectively. The dental floss 20c is supported by a floss support 20d which is provided at an end of the handle 21, and the dental floss 50c is supported by a floss support 50d which is provided at an end of the handle 51. The casing 100 consists of two reception parts 10 and 40. The reception parts 10 and 40 have a hollow box shape for receiving the brush units, and contain gargle 30 and disinfectant 60 therein, respectively. The reception parts 10 and 40 are in close contact with the brush units, at the mouths of the reception parts 10 and 40, to prevent the gargle 30 and the disinfectant 60 from leaking. Further, the two reception parts 10 and 40 are integrated with each other to form a single structure, and are linearly arranged in a straight line in such a way that the mouths of the reception parts 10 and 40 are opposite to each other.

As described above, the present invention provides an interproximal brush, which contains gargle and disinfectant, thus conveniently supplying the gargle and disinfectant to a brushed portion while brushing a gap between neighboring teeth with the interproximal brush. According to this invention, bristles of the interproximal brush are normally soaked with the gargle and the disinfectant, thus preventing bacteria from propagating, conveniently supplying the gargle, such as a mouthwash, and the disinfectant into a brushed portion without an additional gargle injecting device, and thus protecting the gingiva as well as accomplishing an excellent brushing effect.

Further, according to the interproximal brush device of this invention, its reception parts and handles have a square cross-section or a triangular cross-section, so the gargle and the disinfectant are collected on angular corners, thus completely utilizing the gargle and the disinfectant, resulting in effective and economical use. In addition, sales messages or trademarks are easily attached to the sidewall of a casing of the interproximal brush device. Further, it is easy to package the interproximal brush device. And besides, it is possible to receive a plurality of brush units in the interproximal brush device, thus effectively carrying the interproximal brush units.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An interproximal brush device forming a single structure, comprising:
two brush units each consisting of:
a handle having a square cross-section; and
an interproximal cleaning means, having bristles or a dental floss, fixed to an end of the handle; and
a casing consisting of two reception parts, said reception parts having a hollow box shape for receiving said brush units, and containing a gargle and a disinfectant therein, respectively, with a sealing unit being provided at a position around a mouth of each of the two reception parts; and
a packing member having an elastically openable hole, the packing member being provided in each of the two reception parts at a groove formed on an inner circumferential surface of an inside of each reception part, the packing member to be locked to the groove,
wherein the sealing unit consists of a locking ring with a locking groove provided on the inner circumferential surface of the inside of each of the two reception parts where the brush units enter the reception parts, at a position adjacent to the mouth of each reception part, for holding each brushing unit.

2. The interproximal brush device according to claim 1, wherein said two reception parts are integrated with each other to form a single structure, and are linearly arranged in a straight line in such a way that the mouth of each of the reception parts are opposite to each other.

3. The interproximal brush device according to claim 1, wherein said two reception parts are integrated with each other to form a single structure, and are arranged parallel to each other in such a way that the mouth of each of the reception parts are adjacent to each other.

4. The interproximal brush device according to claim 1, wherein said sealing unit comprises:
a locking groove provided on an inner circumferential surface of an inside of each of the two reception parts at a position adjacent to the mouth of each reception part where the brush units enter the reception parts, and holding the brush unit; and
a locking projection provided on an outer circumferential surface of the handle of each brush unit at a midsection thereof.

5. The interproximal brush device according to claim 1, wherein said sealing unit comprises a rubber, said rubber being attached to both the inner circumferential surface of each reception part and the outer circumferential surface of the handle of each brush unit.

6. The interproximal brush device according to claim 1, wherein said sealing unit comprises a silicone, said silicone being attached to both the inner circumferential surface of each reception part and the outer circumferential surface of the handle of each brush unit.

7. The interproximal brushing device according to any one of claims 1 to 6, wherein said gargle and disinfectant contain a substance aiding absorption of calcium.

8. The interproximal brush device according to claim 7, wherein the substance aiding absorption of calcium is Casein Phosphopeptide (CPP).

9. The interproximal brush device according to claim 7, wherein the substance aiding absorption of calcium is Casein Phospho-peptide (CPP-H).

10. The interproximal brush device according to claim 7, wherein the substance aiding absorption of calcium is Casein Phosphopeptide (CPP) and Casein Phospho-peptide (CPP-H).

11. The interproximal brush device according to any one of claims 1 to 6, wherein said disinfectant contains an aromatic substance.

12. The interproximal brush device according to claim 11, wherein the aromatic substance uses an essence selected from the group consisting of mint, fruit and lilac.

13. The interproximal brush device according to any one of claims 1 to 6, wherein said gargle comprises a sterile solution containing a salt roasted in a bamboo.

14. The interproximal brush device according to any one of claims 1 to 6, wherein said gargle comprises a sterile saline solution.

15. The interproximal brush device according to claim 1, wherein the handle of each brush unit has an opening for receiving another brush unit.

16. An interproximal brush device forming a single structure, comprising:
two brush units each consisting of:
a handle having a triangular cross-section;
an interproximal cleaning means, having bristles or a dental floss, fixed to an end of the handle; and
a locking projection provided on an outer circumferential surface of the handle at a midsection thereof;
a casing consisting of two hollow reception parts, said reception parts having a triangular cross-section for receiving said brush units, respectively, and each having a locking groove on an inner circumferential surface of an inside of each of the reception parts where the brush units enter the reception parts, at a position adjacent to a mouth thereof, said locking groove engaging with the locking projection for holding the brush unit, said reception parts also containing gargle and disinfectant therein, respectively; and
a packing member having an elastically openable hole, the packing member being provided in each of the reception parts at a groove formed on the inner circumferential surface of the inside of each of the reception parts, the packing member to be locked to the groove.

17. An interproximal brush device forming a single structure, comprising:
two brush units each consisting of:
a handle having a square cross-section; and
an interproximal cleaning means, having a dental floss supported by a floss support, fixed to an end of the handle; and
a casing consisting of two reception parts, said reception parts having a hollow box shape for receiving said brush units, and containing a gargle and a disinfectant therein, respectively, with a sealing unit being provided at a position around a mouth of each of the two reception parts;
wherein the sealing unit consists of a locking ring with a locking groove provided on the inner circumferential surface of the inside of each of the two reception parts where the brush units enter the reception parts, at a position adjacent to the mouth of each reception part, for holding each brushing unit.

* * * * *